US012778395B2

(12) United States Patent
Lee et al.

(10) Patent No.: US 12,778,395 B2
(45) Date of Patent: Nov. 3, 2026

(54) ENDOSCOPE

(71) Applicant: Medimaging Integrated Solution, Inc., Hsinchu (TW)

(72) Inventors: Chia-Jung Lee, Hsinchu (TW); Yueh-Ying Fan, Hsinchu (TW)

(73) Assignee: Medimaging Integrated Solution, Inc., Hsinchu (TW)

( * ) Notice: Subject to any disclaimer, the term of this patent is extended or adjusted under 35 U.S.C. 154(b) by 405 days.

(21) Appl. No.: 18/482,348

(22) Filed: Oct. 6, 2023

(65) Prior Publication Data

US 2024/0122457 A1 Apr. 18, 2024

(30) Foreign Application Priority Data

Oct. 14, 2022 (TW) ................................. 111139152

(51) Int. Cl.

| | |
|---|---|
| ***A61B 1/005*** | (2006.01) |
| ***A61B 1/018*** | (2006.01) |
| *A61M 25/01* | (2006.01) |

(52) U.S. Cl.

CPC .......... *A61B 1/0052* (2013.01); *A61B 1/0057* (2013.01); *A61B 1/018* (2013.01); *A61M 25/0136* (2013.01); *A61M 25/0147* (2013.01)

(58) Field of Classification Search

CPC ..... A61B 1/0052; A61B 1/0057; A61B 1/018; A61B 1/00066; A61B 25/0136

See application file for complete search history.

(56) References Cited

U.S. PATENT DOCUMENTS

| | | | | |
|---|---|---|---|---|
| 2014/0200402 | A1* | 7/2014 | Snoke | A61B 1/00121 600/104 |
| 2016/0089003 | A1* | 3/2016 | Morimoto | A61B 1/00177 600/107 |
| 2021/0113064 | A1* | 4/2021 | Yoshinaga | A61B 1/0052 |
| 2021/0393113 | A1* | 12/2021 | Matthison-Hansen | A61B 1/0055 |
| 2022/0409028 | A1* | 12/2022 | Akui | A61B 1/018 |
| 2023/0108741 | A1* | 4/2023 | Kawakami | A61B 1/0057 600/146 |
| 2024/0237889 | A1* | 7/2024 | Lee | A61B 1/0057 |

* cited by examiner

*Primary Examiner* — Anhtuan T Nguyen
*Assistant Examiner* — Rynae E Boler
(74) *Attorney, Agent, or Firm* — MUNCY, GEISSLER, OLDS & LOWE, P.C.

(57) ABSTRACT

An endoscope includes a catheter having a lens at one end and extending into a handle, an instrument tube partly received in the handle and partly exposed outside, a linkage unit within the handle, a controlling unit pivotally connected to the linkage unit, a cable connecting the linkage unit and the catheter periphery, a tension unit connected to the cable, and a tension adjusting unit having adjusting members and connection members coupled to the tension unit, thereby enhancing lens control sensitivity and improving instrument insertion and withdrawal smoothness to elevate medical quality.

16 Claims, 8 Drawing Sheets

ENDOSCOPE

BACKGROUND OF THE INVENTION

1. Field of the Invention

The present invention relates to a medical endoscope, particularly to an endoscope with a tension adjusting unit.

2. Description of the Prior Art

The endoscope is a medical instrument, which enters the human body through various channels for observing the internal states of the human body. Although the endoscope only causes a smallest injury to the human body in inspection and surgery, it can achieve the same objectives as the traditional surgery. Hence, the endoscope has become a frequently-used instrument in modern medicine. The endoscope may be applied to the fields of gastrointestinal tracts, respiratory tracts, urinary tracts, female reproductive systems, abdominal cavities, articular cavities, thoracic cavities, etc. The lens steering mechanism of the traditional endoscope includes a rotating wheel inside a handle and an operation rod of the handle connected with the rotating wheel. A cable surrounds the rotating wheel and extends through a snake bone mechanism to a lens. The cable is tensioned or released via the lever principle to control the bending of the snake bone mechanism and turn the direction of the lens.

However, the cable of the traditional endoscope is hard to fix. Such a problem impairs the operation of the lens adjusting mechanism and affects the adjusted angle of the lens. Besides, the traditional endoscope is hard to assemble. Further, the working channel of the traditional endoscope is likely to twist or loosen. Thus, the instrument is often hard to pass the tracts. Such a problem limits the size of the tract the endoscope intends to enter and also limits the selection of the materials.

Therefore, it is learned from the above discussion: the traditional endoscope is unlikely to precisely turn the direction of the lens, and the twist and loosening of the working channel makes the instrument hard to enter the tract smooth. Thus, the medical quality is degraded by the conventional problems.

SUMMARY OF THE INVENTION

In order to overcome the problems of the conventional technology, the present invention provides an endoscope to enhance the agility and accuracy of operating the endoscope and increase the smoothness of introducing and withdrawing the endoscope. The endoscope of the present invention comprises a handle, a catheter, an instrument tube, a linkage unit, a controlling unit, a plurality of cables, a plurality of tension units, and a tension adjusting unit. One end of the catheter is provided with a lens, and the other end of the catheter is extended into the handle. One end of the instrument tube is disposed outside the handle; the other end of the instrument tube is disposed inside the handle. The catheter is connected with and extended from one end of the handle to the other end of the instrument tube. The linkage unit is disposed inside the handle. The controlling unit is disposed outside the handle and corresponding to the linkage unit, and extended in into the handle to be pivotally connected with the linkage unit. Ends of the cables are connected with the linkage unit, and the other ends of the cables are connected to positions between two ends of the catheter. The tension units are disposed in perimeters of the cables. Ends of the tension units are connected to a position of the catheter, which is far away from one end of the handle by a preset distance. The tension adjusting unit includes a plurality of adjusting members and a plurality of connection members. The connection members are connected with the other ends of the tension units and disposed inside the adjusting members.

In a preferred embodiment, the linkage unit includes a body, a first bump, and a second bump; the first bump is disposed on a surface of the body, and a groove is formed between the body and the first bump; the second bump is disposed on the surface of the body; the first bump and the second bump are separated from each other by a given distance, which is determined according to a range of a preset bending angle of the cables; the cables are wound around the groove and extended to the second bump to form a Z-type cable insertion structure.

In a preferred embodiment, the linkage unit includes a plurality of regulation clamps, which is respectively disposed on the surface of the body; the cables are respectively clamped and fixed by at least one of the regulation clamps; each of the regulation clamps includes a first clamp plate and a second clamp plate, which are disposed on the surface of the body; the first clamp plate has a plurality of first protrusions formed on a region, which is between two ends of the first clamp plate; the second clamp plate has a plurality of second protrusions formed on a region, which is between two ends of the second clamp plate and faces the first protrusions; each of the second protrusions is extended to a space between two adjacent first protrusions to form a staggered structure; alternatively, each of the first protrusions is extended to a space between two adjacent second protrusions to form a staggered structure; the cables are inserted into a space between the first protrusions and the second protrusions; the first protrusions and the second protrusions jointly clamp one of the cables.

In a preferred embodiment, the linkage unit further includes a plurality of fixing pillars. The fixing pillars are disposed on a surface of the body. A protrusion is formed on the top of each of fixing pillars. The cables are respectively wound around different fixing pillars. While the linkage unit includes two fixing pillars, the cables are wound around two fixing pillars to-and-fro interweavingly in an 8-shaped route.

In a preferred embodiment, the linkage unit further includes a regulation fender, a first regulation pillar, and a second regulation pillar. The regulation fender is disposed inside the handle and on the edge of the second bump and extended out of the second bump. The first regulation pillar is disposed inside the handle and on the perimeter of the body and defines a first position where the regulation fender is allowed to reach. The second regulation pillar is disposed inside the handle and on the perimeter of the body and defines a second position where the regulation fender is allowed to reach. The distance of the first position and the second position is exactly the preset range by which the controlling unit is allowed to move the cable.

In a preferred embodiment, an instrument tube fender is disposed inside the handle, extended from the instrument tube to one end of the handle. The portion of the instrument tube, which is inside the handle, runs along the instrument tube fender and gradually bends toward one end of the handle.

In a preferred embodiment, the catheter further includes a bendable member, an adapter structure, and an insert member. One end of the bendable member has a lens; another end of the bendable member is connected with one end of the adapter structure. One end of the insert member is connected with another end of the adapter structure; another end of the insert member is connected with another end of the instrument tube.

In a preferred embodiment, the bendable member includes a hose and a plurality of moveable blocks. One end of the hose has a lens; another end of the hose is connected with one end of the adapter structure. The plurality of moveable blocks is disposed on the surface of the hose and connected to each other in series. The cable is inserted through the moveable blocks in sequence and fixed to different positions of the last moveable block.

In a preferred embodiment, the connection members are respectively block bodies; ends of the tension units are respectively fixed to the block bodies; the adjusting member includes a plurality of slots; the slots are disposed inside the handle and respectively at positions, which are between one end of the handle and the linkage unit; the slots respectively accommodates and presses-fit to the block bodies.

In a preferred embodiment, the present invention provides an endoscope, which comprises a handle, a catheter, and an instrument tube. One end of the catheter is extended into one end of the handle; another end of the catheter is extended out of the handle and has a lens. One end of the instrument tube is disposed outside the handle; another end of the instrument tube is disposed inside the handle and has an engagement member. The engagement member is connected with one end of the catheter. The instrument tube has a glue overflow recess on the perimeter of the engagement member.

According to the above description, the present invention has a tension adjusting unit, and the tension unit is fixed to the tension adjusting unit, whereby to control the length of the cable to make the turning angle of the lens more precise. Further, an adapter structure is connected with the insert member and the bendable member to make the catheter less likely to twist, whereby the instrument may pass through the catheter smoother.

The objective, technologies, features and advantages of the present invention will become apparent from the following description in conjunction with the accompanying drawings wherein certain embodiments of the present invention are set forth by way of illustration and example.

BRIEF DESCRIPTION OF THE DRAWINGS

The foregoing conceptions and their accompanying advantages of this invention will become more readily appreciated after being better understood by referring to the following detailed description, in conjunction with the accompanying drawings, wherein.

DESCRIPTION OF THE PREFERRED EMBODIMENTS

Various embodiments of the present invention will be described in detail below and illustrated in conjunction with the accompanying drawings. In addition to these detailed descriptions, the present invention can be widely implemented in other embodiments, and apparent alternations, modifications and equivalent changes of any mentioned embodiments are all included within the scope of the present invention and based on the scope of the Claims. In the descriptions of the specification, in order to make readers have a more complete understanding about the present invention, many specific details are provided; however, the present invention may be implemented without parts of or all the specific details. In addition, the well-known steps or elements are not described in detail, in order to avoid unnecessary limitations to the present invention. Same or similar elements in Figures will be indicated by same or similar reference numbers. It is noted that the Figures are schematic and may not represent the actual size or number of the elements. For clearness of the Figures, some details may not be fully depicted.

Figure 1:
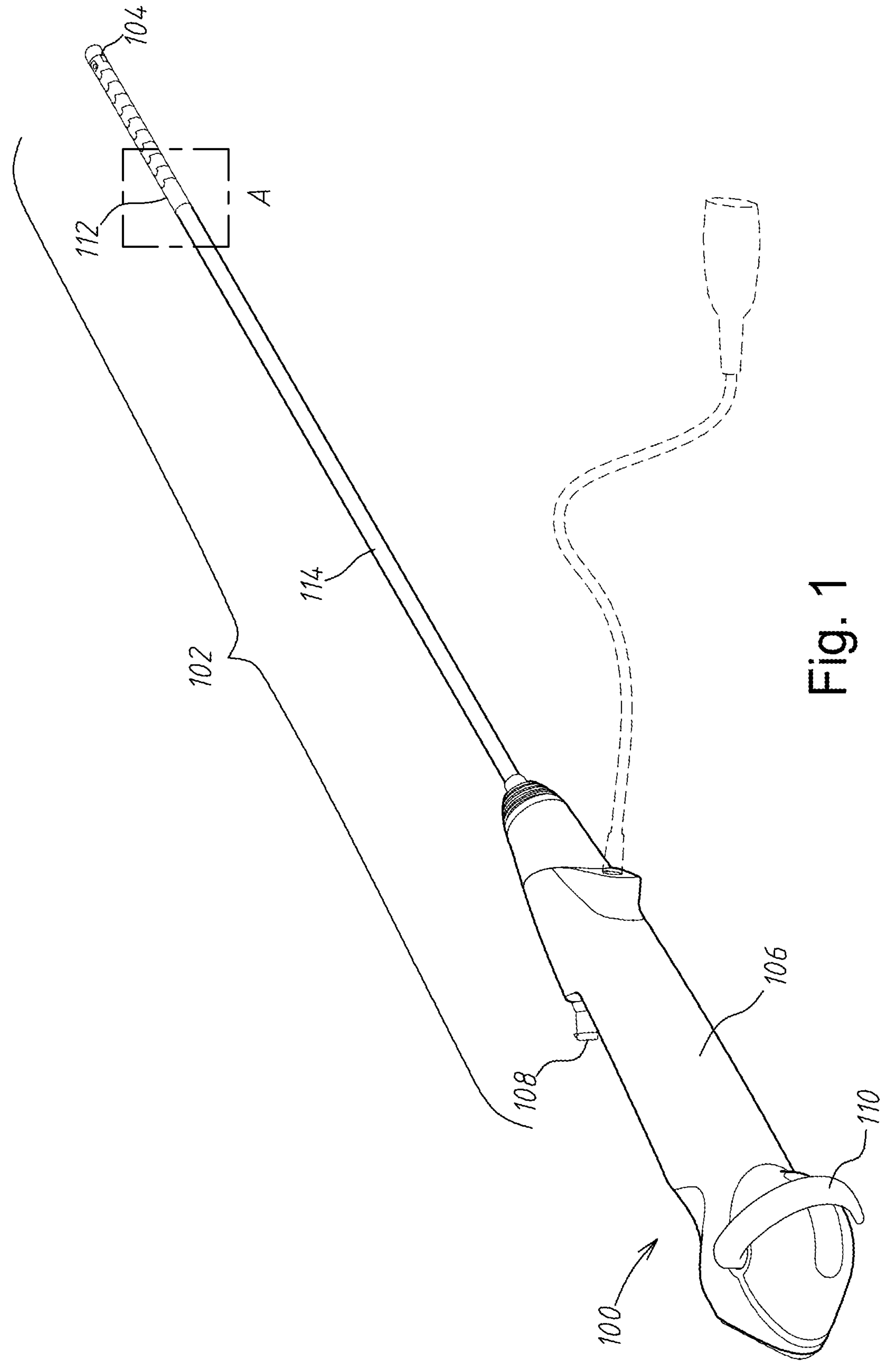
FIG. 1 is a diagram schematically showing an appearance of an endoscope according to one embodiment of the present invention.
Figure 2:
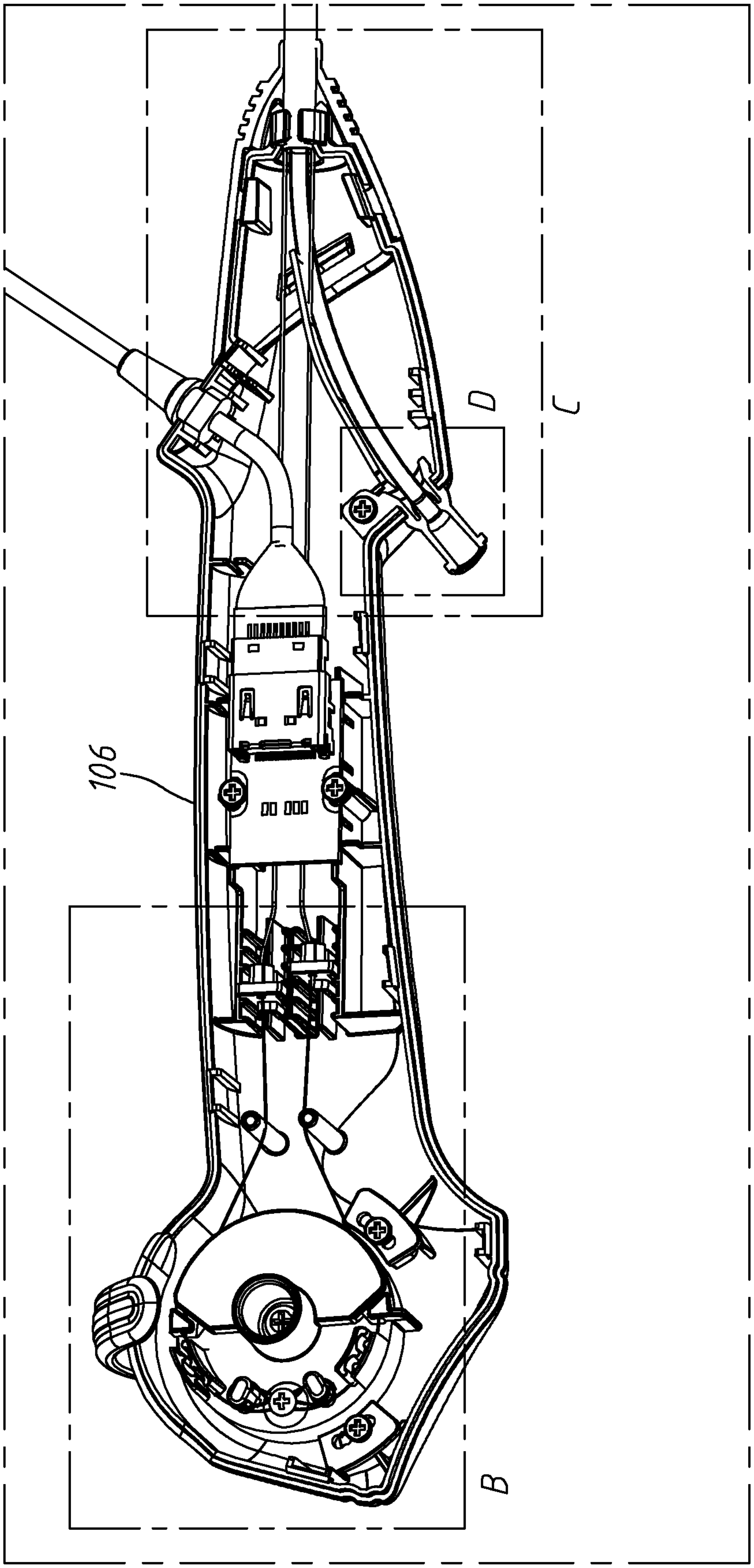
FIG. 2 is a top view schematically showing the interior structure of a handle of an endoscope according to one embodiment of the present invention.
Figure 3:
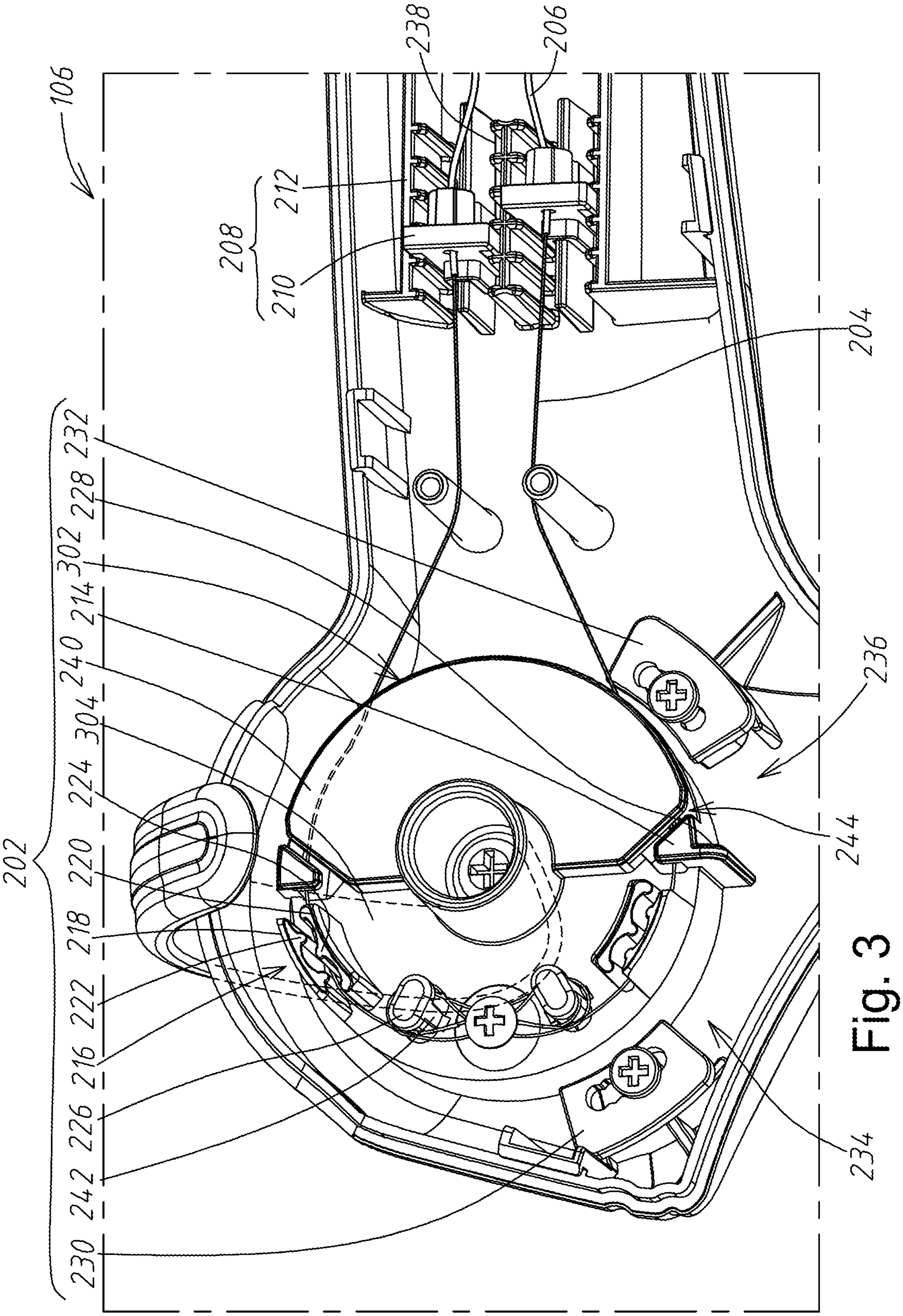
FIG. 3 is a top view schematically showing Part B in FIG. 2.
Figure 4:
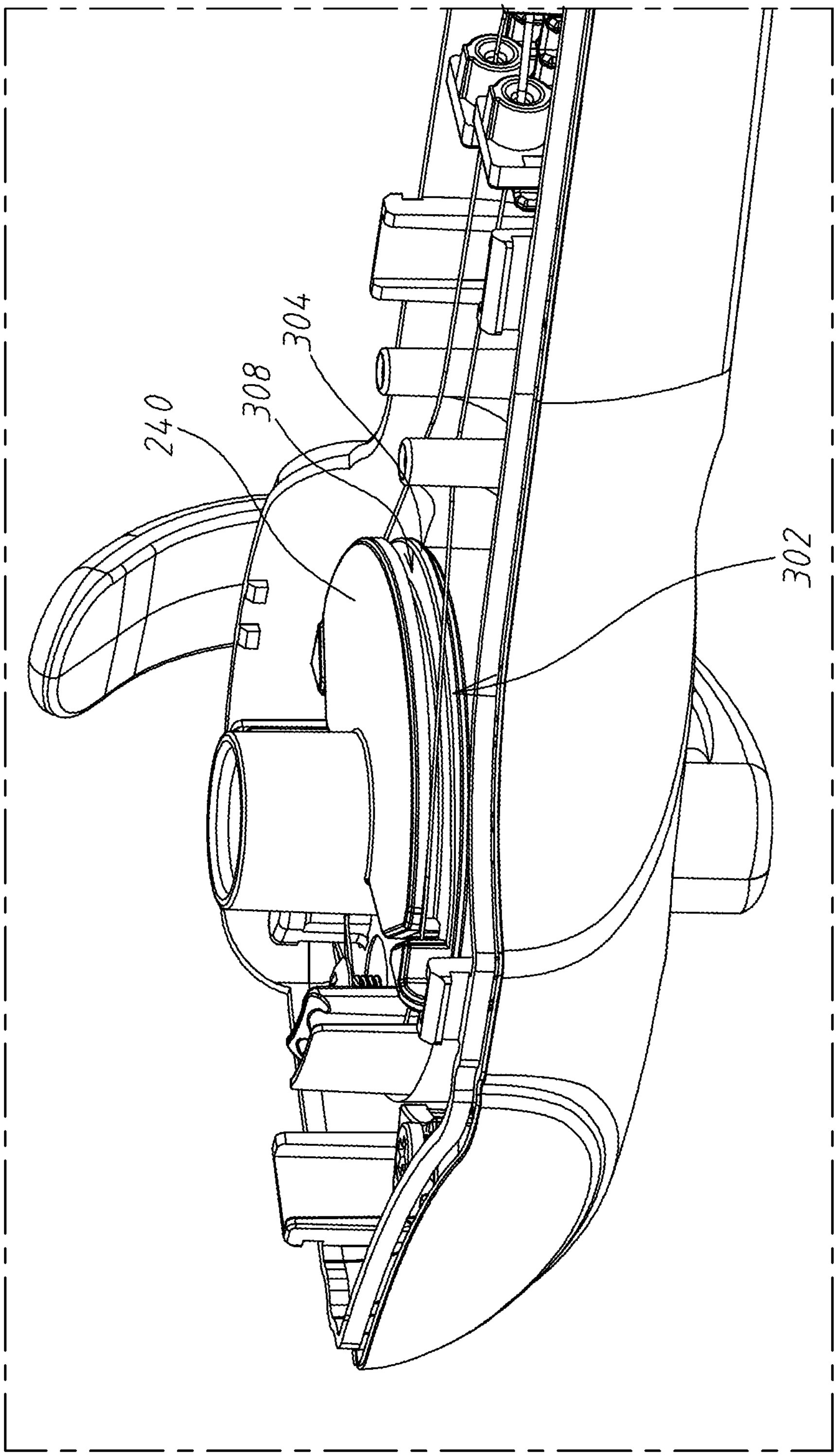
FIG. 4 is a side view schematically showing the structure of a linkage unit of an endoscope according to one embodiment of the present invention.

Refer to FIGS. 1-4. FIG. 1 is a diagram schematically showing an appearance of an endoscope according to one embodiment of the present invention. FIG. 2 is a top view schematically showing the interior structure of a handle of an endoscope according to one embodiment of the present invention. FIG. 3 is a top view schematically showing Part B of the handle in FIG. 2. FIG. 4 is a side view schematically showing the structure of a linkage unit of an endoscope according to one embodiment of the present invention. As shown in FIG. 1, the external structure of the endoscope 100 includes a catheter 102, a handle 106, and a controlling unit 110, wherein the catheter 102 further includes an instrument tube 108, an insert member 114, a bendable member 112, and a lens 104.

FIG. 3 is an enlarged view of Part B in FIG. 2. The handle 106 further includes a linkage unit 202, a plurality of cables 204, a plurality of tension units 206, and a tension adjusting unit 208. The controlling unit 110 may be an operation rod. The controlling unit 110 is disposed at a position of the handle 106, which is corresponding to the linkage unit 202, extended into the interior of the handle 106, and pivotally connected with the linkage unit 202. The linkage unit 202 further includes a body 302, a first bump 240, a second bump 214, a plurality of regulation clamps 216, a plurality of fixing pillars 242, a regulation fender 228, a first regulation pillar 230, and a second regulation pillar 232. The body 302 may be a round disc or a rotating wheel. The tension adjusting unit 208 further includes a plurality of adjusting members 210 and a plurality of connection members 212. The tension unit 206 may be a spring.

Refer to FIG. 3 and FIG. 4. The first bump 240 and the second bump 214 are separated from each other by a given distance, which is determined according to a range of the preset bending angle of the cable 204. A groove 308 exists between the body 302 and the first bump 240. The cable 204 is disposed inside the groove 308. The cable 204 is wound around the groove 308 and extended to the second bump 214 to form a Z-type cable insertion structure 244.

The regulation clamp 216 is disposed on a body surface 304 and includes a first clamp plate 218 and a second clamp plate 220. A plurality of first protrusions 222 is formed between two ends of the first clamp plate 218. A plurality of second protrusions 224 is formed between two ends of the second clamp plate 220. Each of the second protrusions 224 is extended to a space between two adjacent first protrusions 222; each of the first protrusions 222 is extended to a space between two adjacent second protrusions 224, whereby to form a staggered structure. The cable 204 is inserted into a space between the first protrusions 222 and the second protrusions 224 and clamped by the first protrusions 222 and the second protrusions 224.

The fixing pillars 242 are disposed on the body surface 304. A protrusion 226 is formed on the top of each of fixing pillars 242. The cables 204 are respectively wound around different fixing pillars 242. While the linkage unit 202 includes two fixing pillars 242, the cables 204 are wound around two fixing pillars 242 to-and-fro interweavingly in an 8-shaped route.

The regulation fender 228 is formed on the edge of the second bump 214. The regulation fender 228 is an extension of the second bump 214. The first regulation pillar 230 and the second regulation pillar 232 are disposed on the perimeter of the body 302. The first regulation pillar 230 constrains that the regulation fender 228 can only reach a first position 234. The second regulation pillar 232 constrains that the regulation fender 228 can only reach a second position 236. In other words, the distance of the first position 234 and the second position 236 is exactly the preset range by which the controlling unit 110 is allowed to move the cable 204. Although the abovementioned design limits the range of moving the cable 204, it can control the movement of the lens 104 more precisely.

The tension adjusting unit 208 includes the connection members 210 and the adjusting members 212. The adjusting member 212 is disposed between linkage unit 202 and another end of the instrument tube 108. The connection member 210 is a block body. The adjusting member 212 includes a plurality of slots 238. The slots 238 can accommodate and press-fit to the connection members 210. The tension units 206 are fixed inside the connection members 210 and press-fitted to the slots 238 through the connection members 210.

Figure 5:
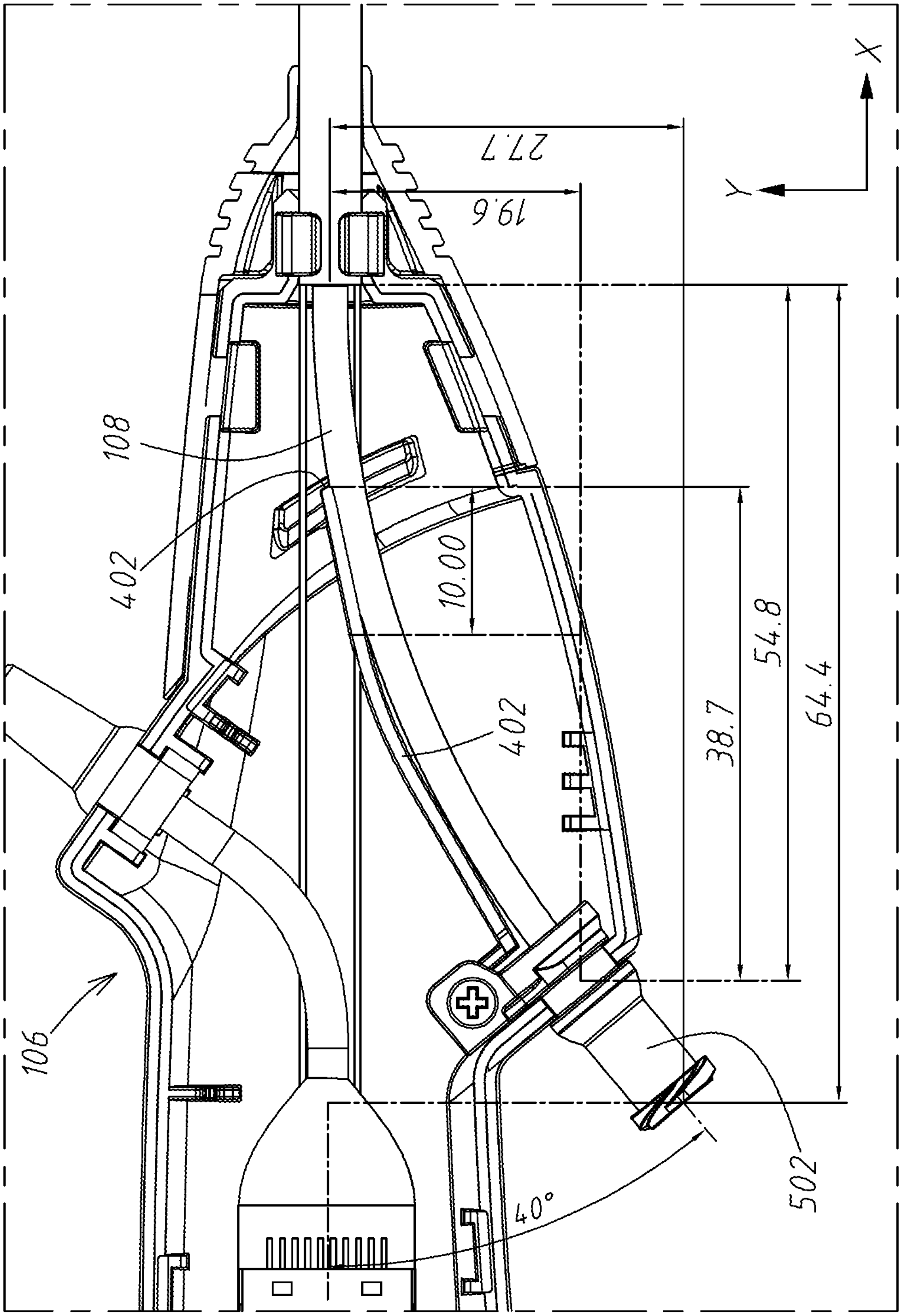
FIG. 5 is a top view schematically showing Part C in FIG. 2.

Refer to FIG. 5. FIG. 5 is a top view schematically showing Part C in FIG. 2. One end of the instrument tube 108 is disposed outside the handle 106; another end of the instrument tube 108 is disposed inside the handle 106; the catheter 102 is connected with the instrument tube 108 inside the handle 106. An instrument tube fender 402 is disposed inside the handle 106, extended from the instrument tube 108 to one end of the handle 106 and gradually bent toward one end of the handle 106. While the user inserts an instrument into the instrument tube 108, the instrument will run inside the instrument tube 108 in compliance with the instrument tube fender 402 to enter the catheter 102.

Figure 6:
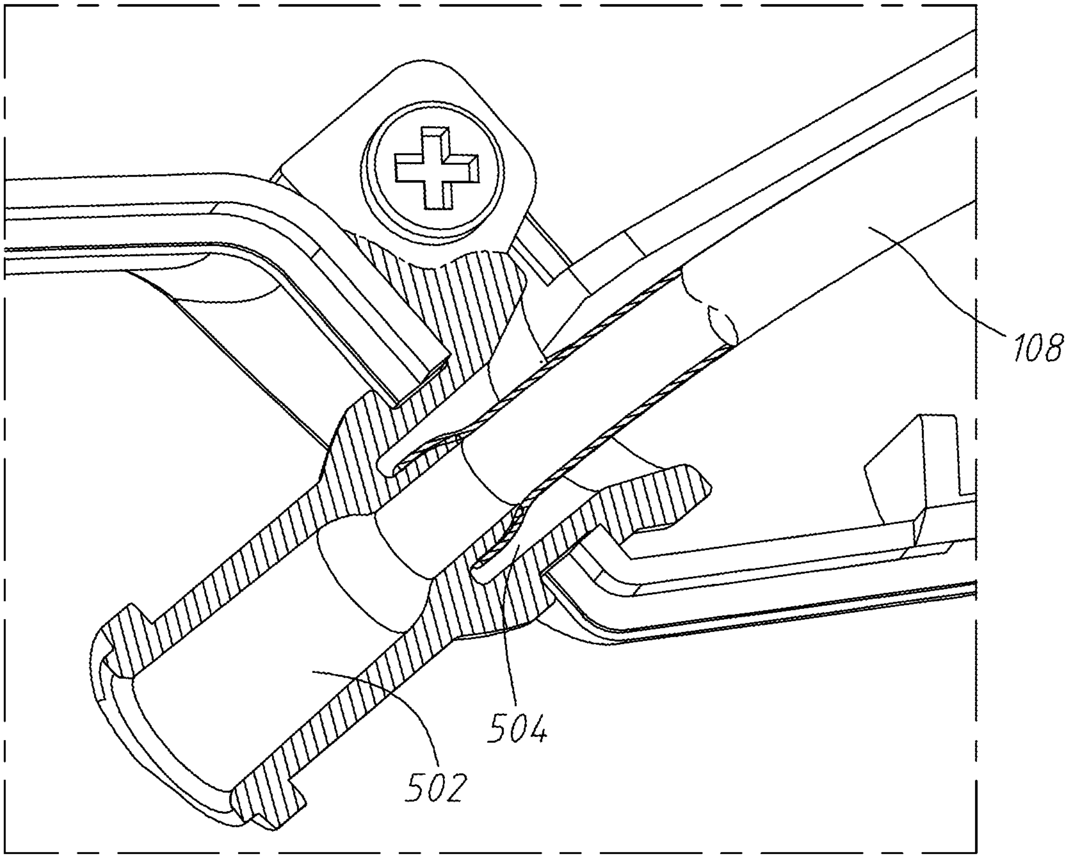
FIG. 6 is a top view schematically showing Part D in FIG. 2.

Refer to FIG. 6. FIG. 6 is a top view schematically showing Part D in FIG. 2. An engagement member 502 is disposed in one end of the instrument tube 108. The engagement member 502 may be a Luer Connector. The engagement member 502 is connected with one end of the catheter 102. The instrument tube 108 has a glue overflow recess 504 to guarantee that the instrument tube 108 is indeed fixed to the correct position and prevent the overflowing glue from blocking the instrument tube 108.

Refer to FIG. 5 again. The included angle between the central axis of the connection member 106 and the central axis of the insert member 114 is 40 degrees. The Y-component of the distance of the engagement member 502 to the center of the insert member 114 is 27.7 mm. The X-component of the distance of the engagement member 502 to the start point of the insert member 114 is 64.4 mm. The Y-component of the distance of the start point of the instrument tube 108 to the center of the handle 106 is 19.6 mm. The X-component of the distance of the start point of the instrument tube 108 to the start point of the insert member 114 is 54.8 mm. The position far away from the start point of the instrument tube 108 by a distance of 38.7 mm in the X-axis direction is the place where the instrument tube 108 is to be bent; the instrument tube fender 402 having a length of at least 10 mm is designed to support the instrument tube 108.

Figure 7:
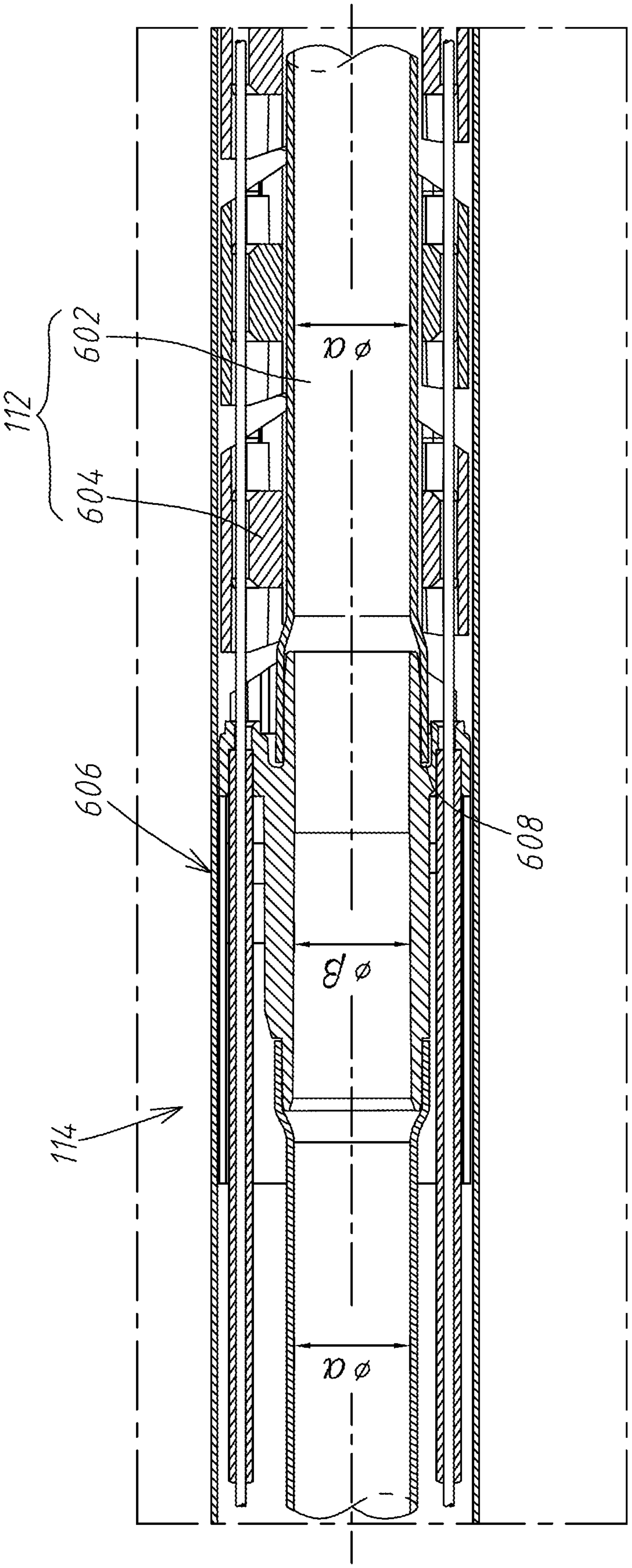
FIG. 7 is a sectional view schematically showing Part A in FIG. 1.
Figure 8:
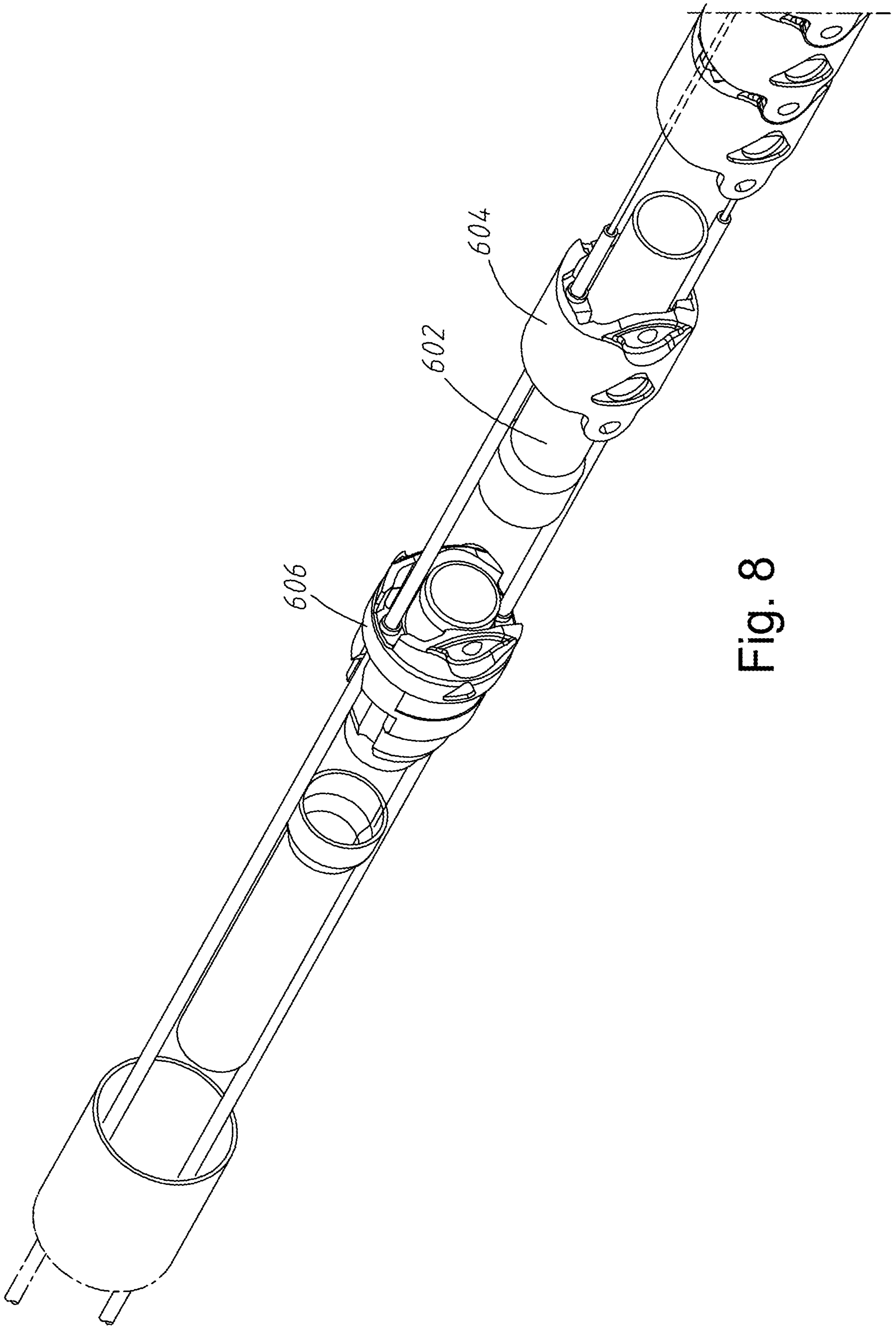
FIG. 8 is an exploded view schematically showing an insert member, an adapter structure and a bendable member according to one embodiment of the present invention.

Refer to FIG. 7 and FIG. 8. FIG. 7 is a sectional view schematically showing Part A in FIG. 1. FIG. 8 is an exploded view schematically showing the insert member, an adapter structure and the bendable member according to one embodiment of the present invention. The bendable member 112, an adapter structure 606 and the insert member 114 are connected in sequence. One end of the bendable member 112 has a lens 104; another end of the bendable member 112 is connected with the adapter structure 606. One end of the insert member 114 is connected with another end of the adapter structure 606; another end of the insert member 114 is connected with the instrument tube 108, wherein the adapter structure 606, the insert member 114 and the instrument member 108 are joined via dispensing glue inside a glue basin 608. The bendable member 112 includes a hose 602 and a plurality of moveable blocks 604. The inner diameter of $øβ$ of the cavity of the adapter structure 606 is greater than or equal to the inner diameter $øα$ of the hose 602. The plurality of moveable blocks 604 is disposed on the surface of the hose 602 and connected in series. At least one cable 204 is inserted through the moveable blocks in sequence and fixed to different positions of the last moveable block 604. The moveable blocks 604 may be snake bone structures. A fixing axis is disposed between the adjacent snake bone structures to stabilize the overall length of the snake bone structures and favor the tension adjusting of the cable 204. As the adapter structure 606 joins together the insert member 114 and the bendable member 112, the catheter 102 is less likely to twist. Therefore, the action of inserting the instrument into the catheter 102 will not be impaired by the twisted catheter. Hence, the instrument will pass through the catheter smoother. Besides, only few hoses 602 are required in the present invention. Thus, the present invention can reduce the fabrication cost.

The present invention uses the controlling unit 110 to control the rotation of the lens 104; the linkage unit 202 moves according to the movement direction of the controlling unit 110; the cable 204 pulls the catheter 102 according to the movement direction of the linkage unit 202; the end of the catheter 102, which is near the lens 104, is bended toward the pulling direction, and the tension unit 206 is simultaneously deformed to generate tension force. In the condition that the controlling unit 110 is released, the tension force of the tension unit 206 will drive the controlling unit 110, the linkage unit 202, the cable 204 and the catheter 102, and restores the controlling unit 110 to the state that the force has not been applied to operate the controlling unit 110.

In the present invention, the tension unit 206 may be fixed to the tension adjusting unit 208, whereby to control the length of the cable 204 and steer the lens 104 more precisely. Further, the adapter structure 606 is arranged between the insert member 114 and the bendable member 112 to make the catheter 106 less likely to twist and make the instrument pass the catheter 102 smoother. Compared with the conventional technology, the present invention can effectively enhance the sensitivity of operating the lens 104 of the endoscope 100 and increase the smoothness of introducing/withdrawing the instrument. Thereby, the medical quality is upgraded.

While the invention is susceptible to various modifications and alternative forms, a specific example thereof has been shown in the drawings and is herein described in detail. It should be understood, however, that the invention is not to be limited to the particular form disclosed, but to the contrary, the invention is to cover all modifications, equivalents, and alternatives falling within the appended claims.

What is claimed is:

1. An endoscope, comprising:

a handle;

a catheter, having a lens at one end thereof, and extended into the handle from one end of the handle;

an instrument tube, wherein one end of the instrument tube is disposed outside the handle; another end of the instrument tube is disposed inside the handle; the catheter is extended between and connected with one end of the handle and another end of the instrument tube;

a linkage unit, disposed inside the handle;

a controlling unit, disposed outside the handle and at a position corresponding to the linkage unit, and extended into the handle to be pivotally connected with the linkage unit;

a plurality of cables, wherein ends of the plurality of cables are connected with the linkage unit; other ends of the plurality of cables are respectively connected to positions between two ends of the catheter;

a plurality of tension units, respectively connected to perimeters of the plurality of cables, wherein ends of the plurality of tension units are connected to a position of the catheter, which is located at a preset distance from one end of the handle; and a tension adjusting unit, including a plurality of adjusting members and a plurality of connection members, wherein the plurality of connection members is respectively connected with other ends of the plurality of tension units; the plurality of adjusting members is respectively disposed inside the handle and on positions, which are between one end of the handle and the linkage unit; the plurality of connection members is respectively moveably disposed at the plurality of adjusting members;

wherein the linkage unit includes:

a body;

a first bump, disposed on a surface of the body, wherein a groove is formed between the body and the first bump;

a second bump, disposed on the surface of the body, wherein the first bump and the second bump are separated from each other by a given distance, which is determined according to a range of a preset bending angle of the cable; the cable is wound around the groove and extended to the second bump to form a Z-type cable insertion structure; and a plurality of regulation clamps, which is respectively disposed on the surface of the body, wherein the plurality of cables is respectively clamped and fixed by at least one of the plurality of regulation clamps;

the at least regulation clamp each includes:

a first clamp plate, disposed on the surface of the body, and having a plurality of first protrusions formed on a region, which is between two ends of the first clamp plate; and a second clamp plate, disposed on the surface of the body, and having a plurality of second protrusions formed on a region, which is between two ends of the second clamp plate and faces the plurality of first protrusions, wherein each of the plurality of second protrusions is extended to a space between two adjacent first protrusions to form a staggered structure; alternatively, each of the plurality of first protrusions is extended to a space between two adjacent second protrusions to form a staggered structure, wherein one of the plurality of cables is inserted into a space between the plurality of first protrusions and the plurality of second protrusions, and the plurality of first protrusions and the plurality of second protrusions jointly clamp one of the plurality of cables.

2. The endoscope according to claim 1, wherein the linkage unit further includes a plurality of fixing pillars, which is disposed on the surface of the body, wherein a protrusion is formed on a top of at least one of the plurality of fixing pillars; the plurality of cables is respectively wound around the plurality of fixing pillars.

3. The endoscope according to claim 2, wherein the linkage unit includes two fixing pillars; at least one of the plurality of cables is wound around the two fixing pillars to-and-fro interweavingly in an 8-shaped route.

4. The endoscope according to claim 1, wherein the linkage unit further includes a regulation fender, formed on an edge of the second bump and extended out of the second bump;

a first regulation pillar, disposed inside the handle and on a perimeter of the body, and defining a first position where the regulation fender is allowed to reach; and a second regulation pillar, disposed inside the handle and on a perimeter of the body, and defining a second position where the regulation fender is allowed to reach, wherein a distance of the first position and the second position is a preset range by which the controlling unit is allowed to move the at least one cable.

5. The endoscope according to claim 1, wherein an instrument tube fender is disposed inside the handle, extended from the instrument tube to an end of the handle; a part of the instrument tube, which is inside the handle, runs along the instrument tube fender and gradually bends toward the end of the handle.

6. The endoscope according to claim 1, wherein the catheter further includes a bendable member, having a lens at one end thereof;

an adapter structure, wherein one end of the adapter structure is connected with another end of the bendable member; and an insert member, wherein one end of the insert member is connected with another end of the adapter structure; another end of the insert member is connected with another end of the instrument tube.

7. The endoscope according to claim 6, wherein the bendable member includes a hose, having a lens at one end thereof, wherein one end of the adapter structure is connected with another end of the hose; and a plurality of moveable blocks, disposed on a surface of the hose, and connected to each other in series, wherein the plurality of cables is inserted through each of the moveable blocks in sequence and fixed to different positions of a last moveable block.

8. The endoscope according to claim 7, wherein the plurality of connection members are respectively block bodies; ends of the plurality of tension units are respectively fixed to the plurality of block bodies; the adjusting member includes a plurality of slots; the plurality of slots is disposed inside the handle and respectively at positions, which are between one end of the handle and the linkage unit; the plurality of slots respectively accommodates and presses-fit to the plurality of block bodies.

9. An endoscope, comprising:
- a handle;
- a catheter, wherein one end of the catheter is extended into one end of the handle; another end of the catheter is extended out of the handle and has a lens; and
- an instrument tube, wherein one end of the instrument tube is disposed outside the handle; another end of the instrument tube is disposed inside the handle and has an engagement member; the engagement member is connected with one end of the catheter; the instrument tube has a glue overflow recess on a perimeter of the engagement member;
- wherein the handle includes:
  - a linkage unit, disposed inside the handle;
  - a controlling unit, disposed outside the handle and at a position corresponding to the linkage unit, and extended into the handle to be pivotally connected with the linkage unit;
  - a plurality of cables, wherein ends of the plurality of cables are connected with the linkage unit; other ends of the plurality of cables are respectively connected to positions between two ends of the catheter; and
  - a plurality of tension units, respectively connected to perimeters of the plurality of cables, wherein ends of the plurality of tension units are connected with a position of the catheter, which is located at a preset distance from one end of the handle;
- wherein the linkage unit includes a plurality of regulation clamps, which is respectively disposed on the surface of the body, wherein the plurality of cables is respectively clamped and fixed by at least one of the plurality of regulation clamps;
- wherein the at least regulation clamp each includes:
  - a first clamp plate, disposed on the surface of the body, and having a plurality of first protrusions formed on a region, which is between two ends of the first clamp plate; and
  - a second clamp plate, disposed on the surface of the body, and having a plurality of second protrusions formed on a region, which is between two ends of the second clamp plate and faces the plurality of first protrusions, wherein each of the plurality of second protrusions is extended to a space between two adjacent first protrusions to form a staggered structure; alternatively, each of the plurality of first protrusions is extended to a space between two adjacent second protrusions to form a staggered structure,
  - wherein one of the plurality of cables is inserted into a space between the plurality of first protrusions and the plurality of second protrusions, and the plurality of first protrusions and the plurality of second protrusions jointly clamp one of the plurality of cables.

10. The endoscope according to claim 9, wherein the linkage unit includes
- a body;
- a first bump, disposed on a surface of the body, wherein a groove is formed between the body and the first bump; and
- a second bump, disposed on the surface of the body, wherein the first bump and the second bump are separated from each other by a given distance, which is determined according to a range of a preset bending angle of the cable; the cable is wound around the groove and extended to the second bump to form a Z-type cable insertion structure.

11. The endoscope according to claim 9, wherein the linkage unit further includes a plurality of fixing pillars, which is disposed on the surface of the body, wherein a protrusion is formed on a top of at least one of the plurality of fixing pillars; the plurality of cables is respectively wound around the plurality of fixing pillars.

12. The endoscope according to claim 11, wherein the linkage unit includes two fixing pillars; at least one of the plurality of cables is wound around the two fixing pillars to-and-fro interweavingly in an 8-shaped route.

13. The endoscope according to claim 9, wherein the linkage unit further includes
- a regulation fender, formed on an edge of the second bump and extended out of the second bump;
- a first regulation pillar, disposed inside the handle and on a perimeter of the body, and defining a first position where the regulation fender is allowed to reach; and
- a second regulation pillar, disposed inside the handle and on a perimeter of the body, and defining a second position where the regulation fender is allowed to reach,
- wherein a distance of the first position and the second position is a preset range by which the controlling unit is allowed to move the at least one cable.

14. The endoscope according to claim 9, wherein an instrument tube fender is disposed inside the handle, extended from the instrument tube to an end of the handle; a part of the instrument tube, which is inside the handle, runs along the instrument tube fender and gradually bends toward the end of the handle.

15. The endoscope according to claim 9, wherein the catheter further includes
- a bendable member, having a lens at one end thereof;
- an adapter structure, wherein one end of the adapter structure is connected with another end of the bendable member; and
- an insert member, wherein one end of the insert member is connected with another end of the adapter structure; another end of the insert member is connected with another end of the instrument tube.

16. The endoscope according to claim 15, wherein the bendable member includes a hose, having a lens at one end thereof, wherein one end of the adapter structure is connected with another end of the hose; and
- a plurality of moveable blocks, disposed on a surface of the hose, connected to each other in series, wherein the plurality of cables is inserted through each of the moveable blocks in sequence and fixed to different positions of a last moveable block.

* * * * *